(12) United States Patent
Keightley et al.

(10) Patent No.: US 7,993,167 B2
(45) Date of Patent: Aug. 9, 2011

(54) SHIELDED ELECTRODE CONNECTOR

(75) Inventors: Leo P. Keightley, Waltham, MA (US);
Daniel F. Mulhauser, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/865,943

(22) PCT Filed: Jan. 28, 2009

(86) PCT No.: PCT/IB2009/050352
§ 371 (c)(1),
(2), (4) Date: Aug. 3, 2010

(87) PCT Pub. No.: WO2009/098613
PCT Pub. Date: Aug. 13, 2009

(65) Prior Publication Data
US 2011/0004090 A1    Jan. 6, 2011

Related U.S. Application Data

(60) Provisional application No. 61/025,862, filed on Feb. 4, 2008.

(51) Int. Cl.
*H01R 4/48* (2006.01)
(52) U.S. Cl. ...................................... 439/729; 439/909
(58) Field of Classification Search ................. 439/729, 439/77, 909, 892
See application file for complete search history.

(56) References Cited

U.S. PATENT DOCUMENTS

| 4,067,342 A |   | 1/1978  | Burton |         |
|-------------|---|---------|--------|---------|
| 4,126,126 A | * | 11/1978 | Bare et al. | 600/392 |
| 4,353,372 A |   | 10/1982 | Ayer |         |
| 4,890,630 A |   | 1/1990  | Kroll et al. |     |
| 6,032,063 A | * | 2/2000  | Hoar et al. | 600/372 |
| 2002/0019166 A1 |   | 2/2002 | Ubby et al. |   |

FOREIGN PATENT DOCUMENTS

EP          0020288 A    12/1980

* cited by examiner

*Primary Examiner* — Javaid Nasri

(57) ABSTRACT

An ECG lead set is described which is shielded against electrostatic charge hazards. An electrical shield is located at the end of each lead of the lead set and electrically shields the connection of the lead set to an ECG electrode. The electrical shield is covered by a nonconductive cover and is electrically connected to the shield of the coaxial cable of the lead set.

10 Claims, 3 Drawing Sheets

SHIELDED ELECTRODE CONNECTOR

This invention relates to medical electrodes for sensing electrical signals from the body and, in particular, to connectors for medical electrodes which are shielded against electrostatic interference.

Medical electrodes can be used for sensing various electrical signal present in the body such as those produced by the heart (electrocardiography) and brain (electro-encephalography). Such bodily signals are very low in intensity and are thus subject to electrical interference from various sources. One such source is electrostatic energy developed by clothing, bedding and from caregivers. A patient's clothing such as sweaters and fleece vests and jackets can generate electrostatic charge. Likewise, electrostatic charge can be generated by blankets and other bedding. A caregiver's body can develop an electrostatic potential which is much greater than that of a patient under the care of the caregiver, resulting in interference as the caregiver approaches the patient. It would therefore be desirable to protect body sensor electrodes from capacitively coupled electronic interference from nearby people and objects of a different electrical potential.

In accordance with the principles of the present invention, a body electrode is provided which is shielded against electrostatic charge hazards. The electrode attaches to the body and is used to sense electrical signals which are processed by a medical instrument such as an electrocardiograph. The electrode is connected to the medical instrument by a lead conductor which is disconnectably coupled to the electrode. An electrical shield is located at the end of the lead conductor which acts to shield the electrical connection when the lead conductor is coupled to the electrode.

Figure 1:
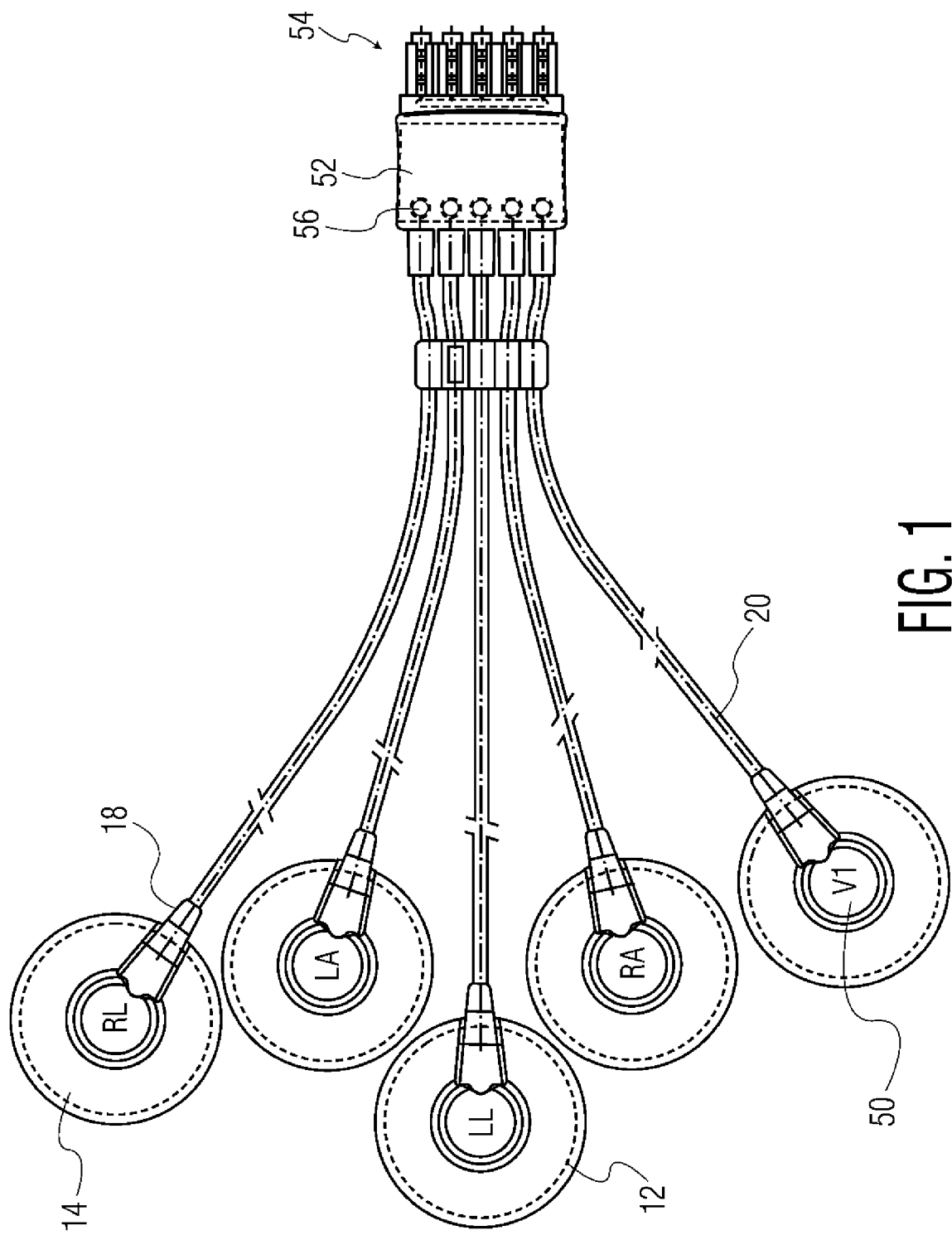
FIG. 1 is a plan view of an electrode lead set with electrostatic shields located at the connector ends of the leads.

Referring first to FIG. 1, a plan view of a five electrode lead set constructed in accordance with the principles of the present invention is illustrated. The illustrated lead set includes five leads 20 with shielded and insulated conductors which couple electrical signals from the body to a medical instrument such as an electrocardiograph (ECG), ECG monitor or defibrillator/monitor. The leads 20 are attached to a connection block 52 where the conductors are electrically attached to a connector block 54. Colored dots 56 on the connection block 52 identify the individual leads for the user. The connector block 54 mates with a trunk cable by which the electrical signals sensed from the body are coupled to the medical instrument.

Located at the distal ends of the leads 20 are shielded connectors which are not visible in this top plan view. Strain reliefs 18 support and strengthen the leads where they are connected to electrode connectors at their distal ends. Located above and extending outward from the central electrode connectors at the end of each lead is a shield 12 contained within a nonconductive dielectric covering 14. The circular dashed line indicated by reference numeral 12 indicates the outer periphery of the electrostatic shield within its dielectric covering. Located at the center of the shielded electrode connectors are labels 50 which identify the locations on the body where each lead is to be connected to an electrode.

Figure 2:
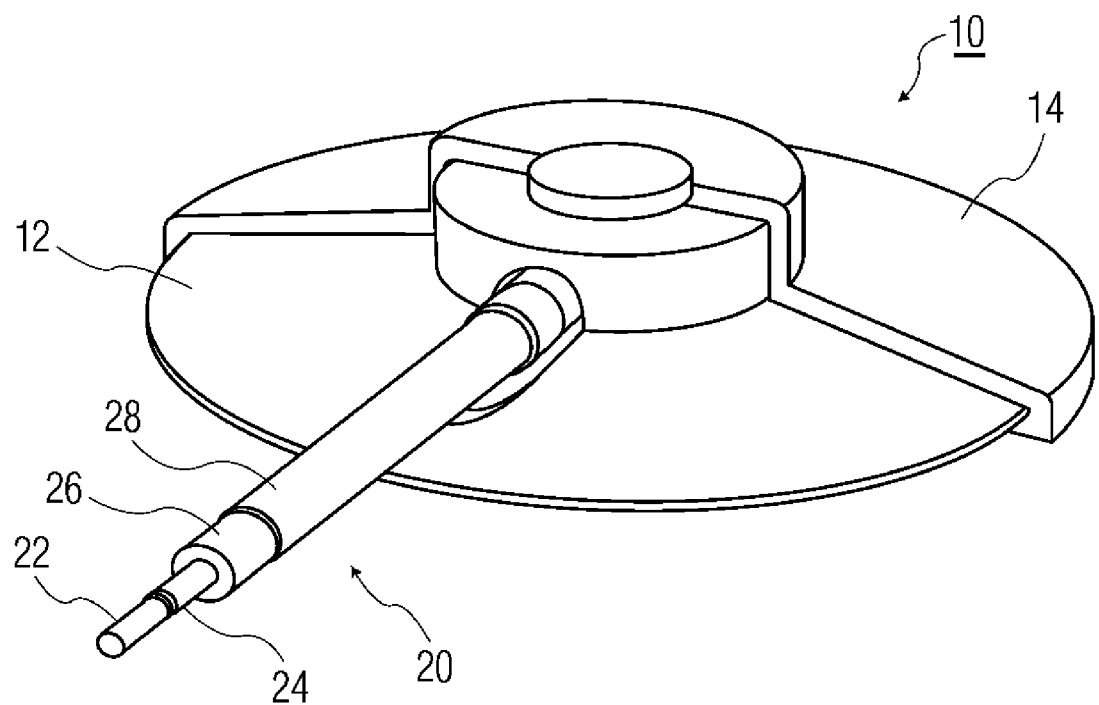
FIG. 2 illustrates in cutaway perspective a view of the top of a shielded lead connector constructed in accordance with the principles of the present invention.

FIG. 2 is a perspective view from above a shielded electrode connector 10 of the present invention at the end of a lead 20. The lead 20 is a coaxial cable consisting of a central signal conductor 22 surrounded by insulation 24. Around the insulated signal conductor is an outer electrical shield 26. The outer shield 26 can be formed of braided wire, a foil wrap, or wound stranded wire. Generally the outer shield will include a drain wire for attachment to electrical elements of the connector which are to be at the electrical potential of the outer electrical shield 26, generally a reference potential. The coaxial lead 20 extends to the center of the connector 10 through an electrically insulated electrode shield 12. In this embodiment the shield 12 covers the dome-shaped center of the connector where the signal conductor is electrically connected to a female snap connector 30a, shown in FIG. 3. The outer shield 26 is electrically connected to the electrode shield 12. The illustrated shield 12 radiates outwardly from the center as a slightly concave disk. The shield 12 is insulated by a nonconductive dielectric cover 14. The cover 14 can be molded around the shield or sandwiched between an upper and a lower dielectric sheet which wraps around or is sealed beyond the periphery of the shield disk 12. In this embodiment the cover 14 is made of a thermoplastic elastomer. The shield 12 can be formed of a foil sheet or conductive paint or other highly conductive material. In this embodiment the shield 12 is formed of a conductive cloth with a conductivity of 1.0 Ohm-cm or less.

Figure 3:
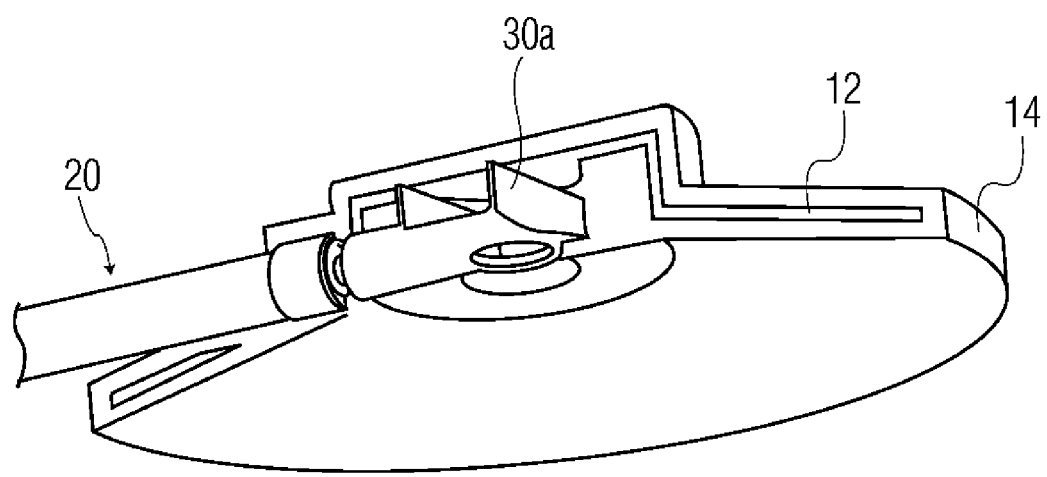
FIG. 3 illustrates in cutaway perspective a view from below the shielded lead connector of FIG. 2.

FIG. 3 is a partially cutaway perspective view of the shielded electrode connector 10 of FIG. 2 from below the connector. This view shows the female snap connector 30a which mates with a male snap connector 30b of an electrode. The shield 12 is seen encapsulated in its dielectric cover 12 which radiates out from the center of the connector 10.

Figure 4:
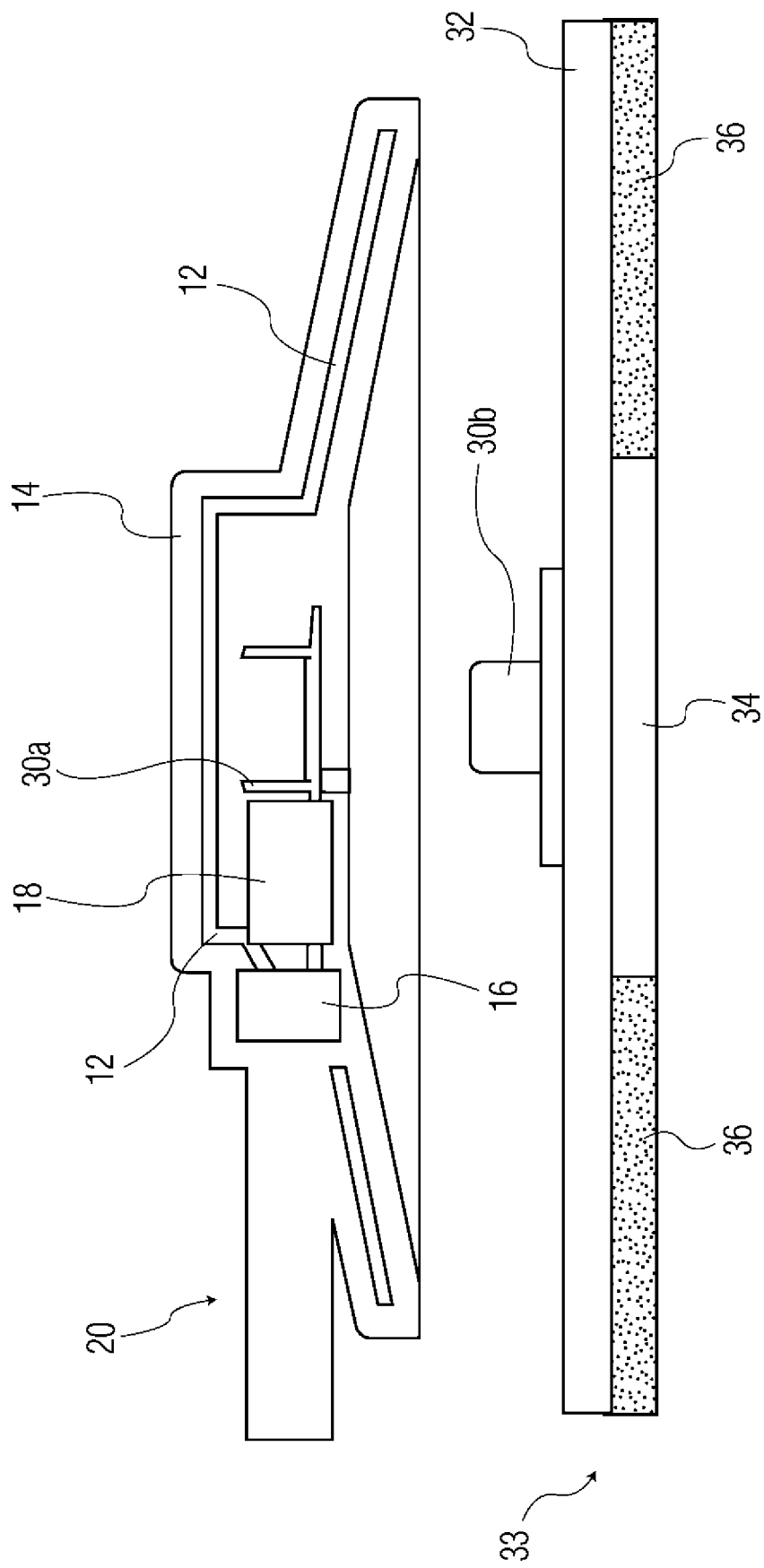
FIG. 4 is a cross-sectional view of the shielded lead connector of FIGS. 2 and 3 located above a mating body electrode.

FIG. 4 is a cross-sectional view of the shielded electrode connector 10 of FIGS. 2 and 3, positioned over a patient electrode 33 to which it connects. In this embodiment the electrical connection of the conductor 22 to the female snap connector 30a is contained within a plastic insulator sleeve 18, which may not be necessary in some embodiments. The outer shield 26 of the coaxial cable 20 is electrically connected to the electrode shield 12 by a copper crimp ring 16. The dome-shaped space in the center of the connector 10 may be made rigid by a hard plastic ring or cap which surrounds the space where the snap connector 30a is located.

The female snap connector 30a attaches to a male snap connector 30b of the patient electrode 33. In this illustration the electrode 33 is a standard ECG electrode part number M2202A, available from Philips Medical Systems of Andover, Mass. The ECG electrode 33 is formed of a disk-shaped plastic film substrate 32. Located on the patient-facing side of the substrate 32 is a central contact electrode 34 made of a gel-soaked foam pad which is electrically conductive. The contact electrode is electrically connected to the male snap connector 30b which is made of a conductive plastic so as to be radiographically transparent. A thin layer of contact adhesive 36 coats the substrate 32 around the contact electrode 34.

In use, when the electrode connector 10 is snapped onto the ECG electrode 33 it can be seen that the electrostatic shield 12 overlays and covers the connection 30a,30b and the contact electrode 34 of the ECG electrode. The shield 12 thus fully shields the connection and the ECG electrode from external electrostatic hazards. Consequently the ECG signals are more noise-free by reason of this shielding.

The dielectric cover 14 insulates the shield 12 and the electrode connection from other external electrical hazards which may arise, such as contact with a defibrillator paddle applied to the patient. For this purpose the cover 14 presents a dielectric strength between the shield 12 and any external conductor of at least 2000 volts DC, and more preferably 5000 volts DC, and most preferably 9000 DC or 6.5K volts AC at 3 kHz.

While the embodiment shown in the drawings is seen to extend the shield out to almost the outer periphery of the patient electrode 33, it will be appreciated that greater or lesser degrees of shielding may be desired in particular applications. For example, a shield which only covers the central area of the electrode, such as the extent of the horizontal section of the shield 12 in FIG. 4, may provide a sufficient amount of shielding for some requirements. The extension of the shield 12 out beyond the central connection area as shown in FIG. 4, beyond the radius of the connection region 30a-30b and the contact electrode 34, will provide an even greater degree of shielding which will be sufficient for many applications.

While the illustrated embodiment shows a snap connector, it will be appreciated that other connectors may alternatively be employed such as a clip-on connector which clips onto a conductive tab on the patient electrode. Other adaptations may be employed to make it easier for the user to see the connection site as the connection is being made, such as to make the radiating insulated shield very flexible so that it can be folded back as connection is being made, or allowing it to slide up the lead 20 as connection is being made.

What is claimed is:

1. A shielded connector for a body electrode comprising:
   a lead having a shielded signal conductor;
   a connector electrically attached to the signal conductor for attachment to a body electrode having a patient-contacting area which conducts received signals to the signal conductor; and
   a conductive electrical shield located above the connector and above the patient-contacting area when the connector is attached to the body electrode, the electrical shield being covered by a nonconductive cover and electrically connected to the shielding of the signal conductor, wherein the conductive electrical shield comprises a unitary disk-shaped shield having an outer periphery extending to a position between the periphery of the patient-contacting area and the outer periphery of the body electrode when the connector is attached to the body electrode.

2. The shielded connector of claim 1, wherein the shielded signal conductor further comprises a coaxial cable having a central signal conductor and an outer shielding conductor, wherein the conductive electrical shield is electrically connected to the outer shielding conductor.

3. The shielded connector of claim 2, wherein the connector is a snap connector.

4. The shielded connector of claim 2, wherein the connector is a clip-on connector.

5. The shielded connector of claim 2, wherein the body electrode further comprises an ECG electrode.

6. The shielded connector of claim 1, wherein the nonconductive cover presents a dielectric strength to an external conductor of at least 2000 volts/mm DC.

7. The shielded connector of claim 1, wherein the nonconductive cover presents a dielectric strength to an external conductor of at least 5000 volts/mm DC.

8. The shielded connector of claim 1, wherein the covered electrical shield extends outward and downward from the connector when the connector is attached to the body electrode.

9. The shielded connector of claim 1, wherein the conductive electrical shield comprises one of a conductive paint, a foil, or a conductive cloth.

10. The shielded connector of claim 9, wherein the conductive electrical shield exhibits a conductivity of 1.0 Ohm-cm or less.

* * * * *